(12) United States Patent
Schelling

(10) Patent No.: US 8,162,996 B2
(45) Date of Patent: Apr. 24, 2012

(54) METHODS FOR REPAIRING BONE DISCONTINUITIES

(75) Inventor: Craig Schelling, Liberty, UT (US)

(73) Assignee: OrthoPro LLC, Salt Lake City, UT (US)

( * ) Notice: Subject to any disclaimer, the term of this patent is extended or adjusted under 35 U.S.C. 154(b) by 255 days.

(21) Appl. No.: 12/607,870

(22) Filed: Oct. 28, 2009

(65) Prior Publication Data

US 2011/0098757 A1    Apr. 28, 2011

(51) Int. Cl.
| | |
|---|---|
| A61B 17/88 | (2006.01) |
| A61B 17/80 | (2006.01) |
| A61B 17/66 | (2006.01) |
| A61B 17/04 | (2006.01) |
| A61B 17/84 | (2006.01) |
| A61F 2/08 | (2006.01) |

(52) U.S. Cl. ........ 606/281; 606/280; 606/282; 606/300; 606/324; 606/286

(58) Field of Classification Search .................. 606/324, 606/280, 281, 282, 286
See application file for complete search history.

(56) References Cited

U.S. PATENT DOCUMENTS

| | | | |
|---|---|---|---|
| 3,528,085 A | 9/1970 | Reynolds | |
| 4,408,601 A | 10/1983 | Wenk | |
| 5,746,741 A | 5/1998 | Kraus | |
| 5,968,046 A * | 10/1999 | Castleman | 606/286 |
| 6,692,503 B2 | 2/2004 | Foley et al. | |
| 6,746,449 B2 | 6/2004 | Jones et al. | |
| 6,916,320 B2 | 7/2005 | Michelson | |
| 7,090,674 B2 | 8/2006 | Doubler et al. | |
| 7,090,676 B2 | 8/2006 | Huebner et al. | |
| 7,537,596 B2 | 5/2009 | Jensen | |
| 7,537,604 B2 | 5/2009 | Huebner | |
| 7,914,536 B2 | 3/2011 | MacDonald et al. | |
| 2002/0120273 A1 | 8/2002 | Needham et al. | |
| 2002/0188297 A1 | 12/2002 | Dakin et al. | |
| 2004/0220571 A1 * | 11/2004 | Assaker et al. | 606/69 |
| 2005/0277941 A1 | 12/2005 | Trumble et al. | |
| 2006/0217735 A1 | 9/2006 | MacDonald | |

(Continued)

FOREIGN PATENT DOCUMENTS

DE    4127303    2/1993

OTHER PUBLICATIONS

Orthohelix, MaxLock Extreme Innovative Plate and Screw System, Copyright 2009, pp. 1-14, Medina, OH, available, on information and belief, at least as early as Sep. 22, 2009.

(Continued)

*Primary Examiner* — Thomas C. Barrett
*Assistant Examiner* — Christine Nelson
(74) *Attorney, Agent, or Firm* — Workman Nydegger

(57) ABSTRACT

A compression plate kit that allows for manual compression of a bone discontinuity includes a bone plate, two or more reduction screws, and a compression clamp. The compression clamp can include engagement members configured to engage the reduction screws, thereby allowing a practitioner to compress a bone discontinuity by manually closing the compression clamp. One or more implementations of a kit of the present invention can provide a practitioner with physical or tactile feedback during the compression of a bone discontinuity, and thus, provide the practitioner with the ability to better control the compression and spacing of bone portions during a reduction.

42 Claims, 7 Drawing Sheets

U.S. PATENT DOCUMENTS

| | | | |
|---|---|---|---|
| 2007/0270850 A1* | 11/2007 | Geissler | 606/69 |
| 2009/0210010 A1 | 8/2009 | Strnad et al. | |
| 2009/0210011 A1 | 8/2009 | Den Hartog et al. | |
| 2009/0210013 A1 | 8/2009 | Kay et al. | |

OTHER PUBLICATIONS

Wright Medical Technology, Inc., Charlotte, Copyright 2007, pp. 1-20, Arlington, TN.

Wright Medical Technology, Inc., Locon-T Surgical Technique, Copyright 2005, pp. 1-12, Arlington, TN.

European Patent Office, English Translation of Abstract for DE4127303 (1 page).

Brochure entitled "2.4 mm/2.7 mm Variable Angle LCP Forefoot/Midfoot System," copyright 2010 (95 pages).

Brochure entitled "Aesculap Spine—Casper Cervical Retractor System," copyright 2009 (16 pages).

U.S. Appl. No. 13/075,871 entitled Compression Plate Kit and Methods for Repairing Bone Discontinuities, filed Mar. 30, 2011, including filing receipt, specification and drawings (76 pages).

International Search Report and Written Opinion from PCT/US2010/053681 dated Dec. 21, 2010, 10 pages.

Brochure entitled "Aesculap Spine—Socon," available upon information and belief at least as early as 2007 (20 pages).

Website pages from www.aesculapimplantsystems.com, copyright 2011, printed May 24, 2011, (3 pages).

Illustrations of Aesculap Socon Spinal Fixation System, which were available, upon information and belief, at least as early as Mar. 2010 (2 images, 1 page).

Website page from www.braun.com, copyright 2011, printed May 24, 2011 (1 page).

Spine and Spine, Global Spine Products Overview, pp. 1-212, document available at www.spineandspine.com/old/pdf/019.pdf, available, on information and belief, at least as early as May 15, 2007.

Wright Medical Technology, Inc., Foot and Ankle Products, pp. 1-20, documents available under links found at http://www.wmt.com/footandankle/bytype.asp, available, on information and belief, at least as early as Sep. 22, 2009.

* cited by examiner

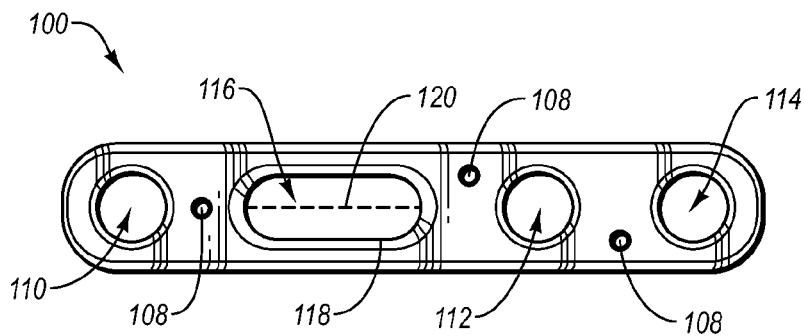
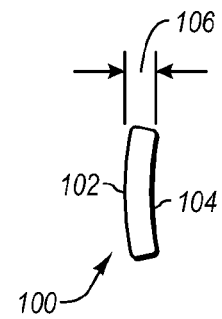
Figure 1A
Figure 1B
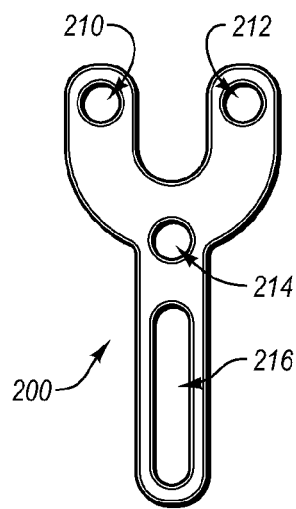
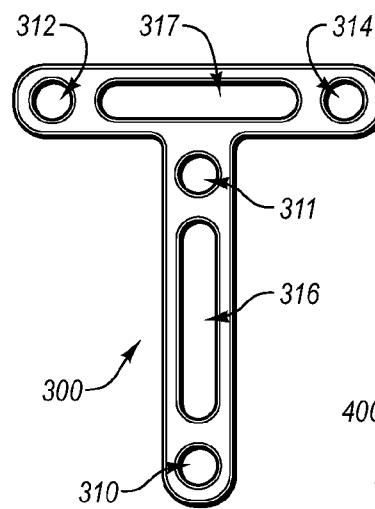
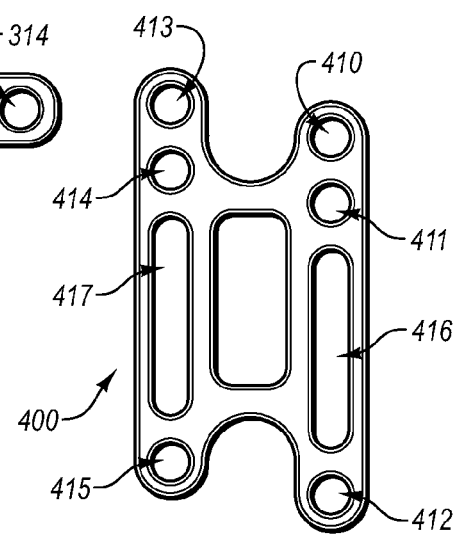
Figure 2
Figure 3
Figure 4

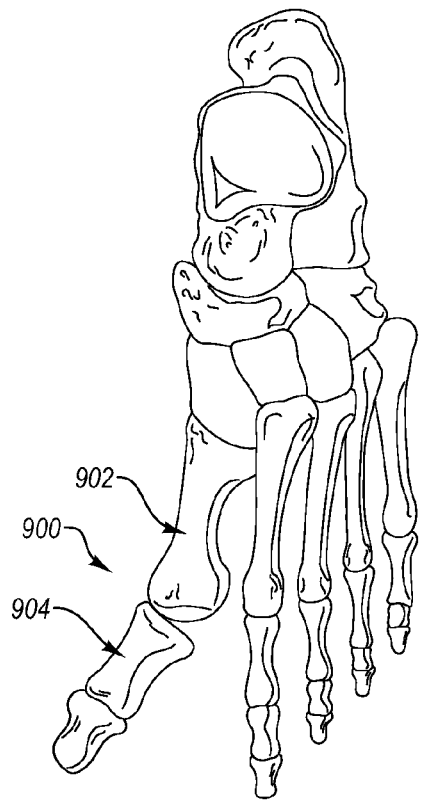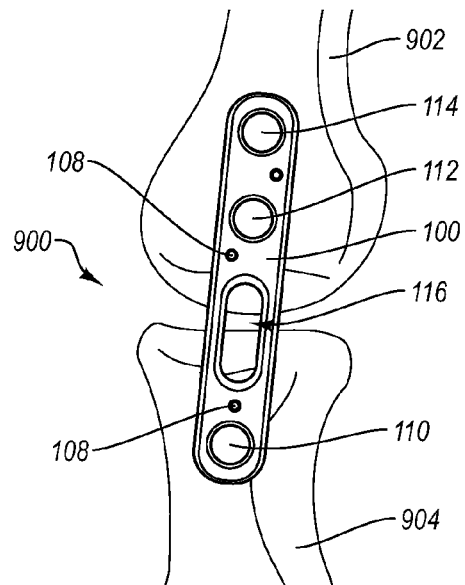
Figure 10A
Figure 9
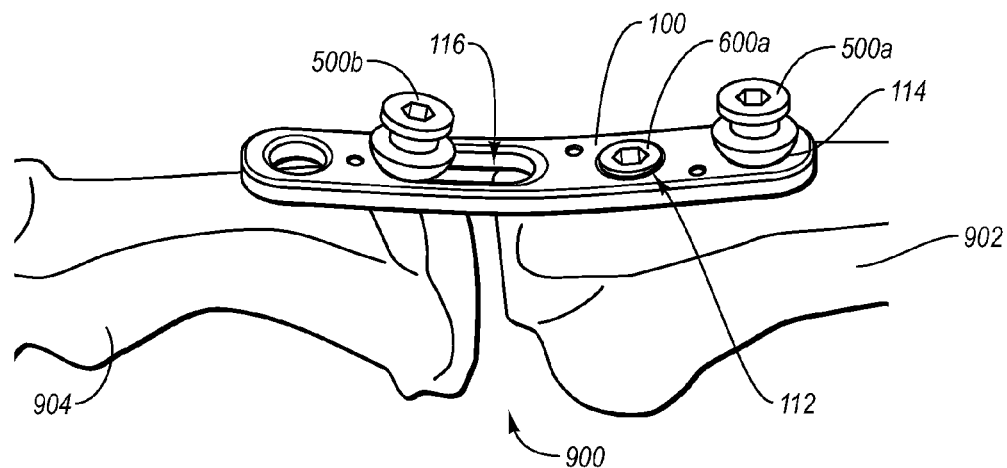
Figure 10B

METHODS FOR REPAIRING BONE DISCONTINUITIES

BACKGROUND OF THE INVENTION

1. The Field of the Invention

The present invention relates generally to a kit for repairing bones. More specifically, the invention relates to a compression plate kit configured to permit manual reduction of bone discontinuities and methods of using the compression plate kit for repairing bone discontinuities.

2. Background and Relevant Art

Bones perform a variety of important functions, including support, movement, protection, storage of minerals, and formation of blood cells. To help ensure that bones can perform these important functions, and to reduce pain or correct disfigurement, injured bones should be promptly and properly repaired. In repairing fractured or otherwise injured bones, it is common for a practitioner to use a fixation device that both reinforces the bone and keeps it properly aligned during healing. One common type of fixation device is a bone plate.

To use a bone plate to repair a discontinuity of a bone, a practitioner typically (1) selects an appropriate plate, (2) reduces the discontinuity (e.g., sets the fracture), and (3) fastens the plate to the bone. The plate is usually secured to bone portions disposed on opposing sides of the discontinuity using suitable fasteners, such as screws and/or wires, so that the bone portions are fixed in proper alignment. It is often important to reduce a bone discontinuity to help ensure proper alignment, and thereby decrease pain, prevent later deformity, and help allow the bone to heal properly and quickly.

One aspect of reducing a bone discontinuity involves compressing bone portions on opposing sides of the discontinuity together and/or otherwise adjusting the bone portions to help ensure proper spacing, or lack thereof, prior to fixation of the bone plate. Ensuring proper spacing between opposing bone portions of a discontinuity can be particularly important because in some cases any space between the two bones can result in prolonged healing and complete ossification of the gap between the bones. Such changes to the shape of the bone can alter the mechanics of the bone in a manner that could weaken or result in changes to the biomechanics of the patient's body. Additionally, such spacing can result in abnormal growth in the bone that can create additional complications. To aid in reducing bone discontinuities, some bone plates, called compression plates, not only secure bone fragments or portions together, but also impart relative movement between the bone portions to help ensure the bone portions are properly spaced and aligned.

Specifically, compression plates typically include fixation holes and a compression slot (a tapered or inclined slot that causes a screw to move from one end to the other as the screw is tightened). To use a compression plate, a practitioner attaches the compression plate to one side of the bone discontinuity using one or more fasteners. The practitioner then inserts a screw within the compression slot, as far from the discontinuity as possible, and begins tightening the screw within the compression slot. During tightening, the head of the screw engages the tapered or inclined surfaces of the compression slot causing the screw, and the bone portion(s) connected thereto, to move along the compression slot, thereby compressing bone portions on opposing sides of the discontinuity together.

Unfortunately, conventional compression plates tend to suffer from a number of drawbacks. For example, the length of conventional compression slots, and thus the amount of compression provided thereby, is limited by the size and shape of the head of the screw being used therewith. Thus, most conventional compression plates allow for a compression of 2 millimeters for less. Furthermore, controlling the exact amount of compression or spacing between bone portions using conventional compression plates can be difficult. Specifically, the amount of compression generated between two bone portions using a conventional compression plate is based on the initial positioning of the screw within the compression slot and on how tight the screw is fixed within the compression slot; neither of which provide any quantifiable feedback to the practitioner on the actual amount of compression between bone portions. Thus, a practitioner is often forced to make an educated guess on the exact compression between portions of a bone discontinuity when using conventional compression plates.

BRIEF SUMMARY OF THE INVENTION

Implementations of the present invention solve one or more of the foregoing problems in the art with systems, methods, and apparatus that provide a great deal of functional versatility in correcting bone discontinuities. For example, one or more implementations of the present invention includes a compression plate kit that allows for manual compression control of a bone discontinuity for improved repair of fractures, fusions, and other bone discontinuities. Additionally, one or more implementations of the present invention includes compression plate kits that allow for the compression of larger gaps between bones. Accordingly, implementations of the present invention can allow for efficient and accurate correction of various different types of bone injury.

For example, one implementation of a surgical kit for use in correcting a discontinuity between a first bone portion and a second bone portion includes a bone plate having one or more fixation holes and at least one elongated slide channel. The kit further includes two or more reduction fasteners each having a head and a threaded shaft. A first reduction fastener is adapted to be inserted within a fixation hole of the bone plate, and a second reduction fastener is adapted to be inserted within the at least one elongated slide channel. Additionally, the kit includes a compression clamp having a pair of engagement members adapted to engage the heads of the first and second reduction fasteners. The compression clamp draws the second reduction fastener along the at least one elongated slide channel toward the first reduction fastener, thereby compressing a bone discontinuity.

Another implementation of a kit for use in correcting bone discontinuities includes a bone plate adapted to secure a first bone portion to a second bone portion. The bone plate has a first fixation hole, an elongated slide channel, and a second fixation hole. The kit further includes a first reduction fastener having a first head including a first engagement groove extending radially therein. The first reduction fastener is adapted to be inserted within the second fixation hole of the bone plate and secured to the first bone portion. The kit also includes a second reduction fastener having a second head including a second engagement groove extending radially therein. The second reduction fastener is adapted to be inserted within the elongated slide channel of the bone plate and secured to the second bone portion. Additionally, the kit includes a compression clamp having a first hook and a second hook. The first hook is sized and configured to be at least partially inserted within the first engagement groove and engage the first head of the first reduction fastener. The second hook is sized and configured to be at least partially inserted within the second engagement groove and engage the second head of the second reduction fastener. The compression clamp is thus configured to draw the second reduction fastener along the elongated slide channel of the bone plate toward the first reduction fastener, thereby pulling the second bone portion toward the first bone portion.

In addition to the foregoing, an implementation of a method of surgically repairing a bone discontinuity involves securing a first reduction fastener within a first fixation hole of a bone plate and to a first bone portion. The method also involves securing a second reduction fastener within an elongated slide channel of the bone plate and to a second bone portion. Additionally, the method involves positioning a first engagement member of a compression clamp about a head of the first reduction fastener. The method further involves positioning a second engagement member of the compression clamp about a head of the second reduction fastener. Also, the method involves closing the compression clamp, thereby drawing the second reduction fastener and the second bone portion along the elongated slide channel toward the first reduction fastener and the first bone portion. The method additionally involves securing a fixation fastener within a second fixation hole of the bone plate and to the second bone portion.

Additional features and advantages of exemplary implementations of the invention will be set forth in the description which follows, and in part will be obvious from the description, or may be learned by the practice of such exemplary implementations. The features and advantages of such implementations may be realized and obtained by means of the instruments and combinations particularly pointed out in the appended claims. These and other features will become more fully apparent from the following description and appended claims, or may be learned by the practice of such exemplary implementations as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. It should be noted that the figures are not drawn to scale, and that elements of similar structure or function are generally represented by like reference numerals for illustrative purposes throughout the figures. Understanding that these drawings depict only typical embodiments of the invention and are not therefore to be considered to be limiting of its scope, the invention will be described and explained with additional specificity and detail through the use of the accompanying drawings in which:

FIG. 1A illustrates a plan view of a bone plate in accordance with an implementation of the present invention;

FIG. 1B illustrates an end view of the bone plate of FIG. 1A;

FIG. 2 illustrates a plan view of another bone plate in accordance with an implementation of the present invention;

FIG. 3 illustrates a plan view of an additional bone plate in accordance with an implementation of the present invention;

FIG. 4 illustrates a plan view of yet another bone plate in accordance with an implementation of the present invention;

FIG. 9 illustrates a top perspective-view of an exemplary bone discontinuity, specifically a dislocation of a metatarsophalangeal joint;

FIG. 10A illustrates the bone plate of FIGS. 1A-1B in an exemplary operating environment, depicting the bone plate placed about the exemplary bone discontinuity of FIG. 9 in accordance with an implementation of the present invention;

FIG. 10B illustrates the bone plate of FIG. 10A secured to the portions of the exemplary bone discontinuity via the fixation fastener of FIG. 6 and a pair of reduction fasteners of FIG. 5;

DETAILED DESCRIPTION OF THE PREFERRED EMBODIMENTS

Figure 5:
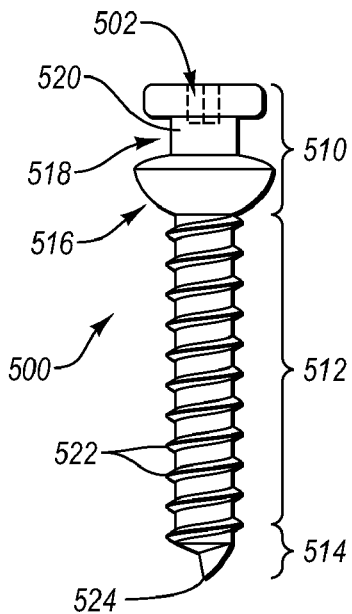
FIG. 5 illustrates a side perspective-view of a reduction fastener in accordance with an implementation of the present invention.

Implementations of the present invention provide systems, methods, and apparatus that provide a great deal of functional versatility in correcting bone discontinuities. For example, one or more implementations of the present invention includes a compression plate kit that allows for manual compression control of a bone discontinuity for improved repair of fractures, fusions, and other bone discontinuities. Additionally, one or more implementations of the present invention includes compression plate kits that allow for the compression of larger gaps between bones. Accordingly, implementations of the present invention can allow for efficient and accurate correction of various different types of bone injury.

For instance, according to one implementation of the present invention, a compression plate kit allows a practitioner to not only manually control the compression and reduction of a bone discontinuity, but to also feel and/or see the amount of compression. The ability to feel and/or see the amount of compression can allow the practitioner to properly set the spacing and alignment between bone portions of a bone discontinuity, and thereby help ensure proper healing. In other words, one or more implementations of the present invention provide a practitioner with physical or tactile feedback during the compression of a bone discontinuity, and thus, provide the practitioner with the ability to better control the compression and spacing of bone portions during a reduction.

More particularly, one or more implementations of a bone plate kit of the present invention include a bone plate, one or more fasteners, and a compression clamp. The bone plate is adapted to be secured to opposing bone portions of a bone discontinuity via a pair of reduction fasteners. A first reduction fastener is adapted to be secured within an elongated slide channel of the bone plate and to a first portion of the bone discontinuity. The second reduction fastener is adapted to be secured within a fixation hole of the bone plate and to a second portion of the bone discontinuity. The compression clamp is adapted to engage the reduction fasteners. After engaging the reduction fasteners with the compression clamp, a practitioner closes the compression clamp, thereby drawing the second reduction fastener (and the second bone portion secured thereto) along the elongated slide channel toward the first reduction fastener (and the first bone portion secured thereto). Because the amount of force the practitioner applies to the compression clamp controls the amount of compression between the bone portions of the bone discontinuity, the bone plate kit provides the practitioner with physical feedback on the distance reduced and the amount of compression between the bone portions of a bone discontinuity.

As previously mentioned, one or more implementations of the present invention are directed towards a compression plate kit and methods of using such a kit to repair bone fractures, fusions, and other bone discontinuities. The various elements of a kit in accordance with one or more implementations will be described with reference to FIGS. 1A-8; after which an exemplary surgical method of repairing a bone discontinuity using a compression plate kit of the present invention will be described with references to FIGS. 9-10F.

FIGS. 1A and 1B, and the corresponding text, illustrate or describe an exemplary bone plate 100 of a compression plate kit according to one or more implementations of the present invention. As an initial matter, bone plates in accordance with one or more implementations of the present invention generally comprise a relatively low-profile (or plate-like) fixation device configured to stabilize a bone discontinuity by attachment to bone portions on opposing sides thereof. For example, the bone plate 100 is configured to span a bone discontinuity (such as, for example, a fracture, a cut, or a bone joint) so that the bone plate 100 fixes the relative positions of bone portions disposed on opposing sides of the bone discontinuity. The bone plate 100 is generally configured to contact an outer surface of the bone, and thus, may be positioned at least substantially exterior to the bone. The bone plate 100 may be left in place permanently or removed after the associated bone discontinuity has partially or completely healed.

The bone plate 100 has a structurally sturdy yet configurable construction. For example, the bone plate 100 is stiff and strong enough to provide support to opposing portions of a bone discontinuity, yet flexible (e.g., resilient) enough to avoid significantly straining the bone. The bone plate 100 may comprise biocompatible materials such as, for example, titanium or titanium alloys, cobalt chromium, stainless steel, polymers, or ceramics, and/or bioabsorbable materials. In any case, the bone plate 100 is configured to reduce irritation to the bone and surrounding tissue. For example, as previously mentioned, the bone plate 100 has a low profile to reduce protrusion into adjacent tissues.

As shown in FIG. 1B, the bone plate 100 includes a distal (bone-opposing) surface 102 and a proximal (bone-facing) surface 104. One or both of the distal 102 and proximal 104 surfaces can optionally be contoured or otherwise configured to correspond with a surface of a target bone (or bones), so that the bone plate 100 maintains a low profile and fits onto the bone(s). For example, the proximal surface 104 of the bone plate 100 may be generally complementary in contour to the surface of a bone.

The thickness 106 of the bone plate 100 is defined by the distance between the proximal 104 and distal 102 surfaces of the bone plate 100. In some implementations of the present invention, the thickness 106 of the bone plate 100 varies along the length of the bone plate 100. For example, portions of the bone plate 100 configured to extend over a tuberosity or the like may have a smaller thickness, thereby reducing profile and/or rigidity. Additionally, the thickness 106 of the bone plate 100 may differ depending upon the intended use of the bone plate 100. For example, a thinner bone plate 100, such as that shown in FIGS. 1A-1B, is configured for use on smaller bones and/or on bones or bone regions where soft tissue irritation is a greater concern.

Additionally, the thickness 106 of the bone plate 100 also may be configured to allow for further contouring and bending of the bone plate 100. For example, the thickness of the bone plate 100 shown in FIGS. 1A and 1B allows a practitioner to use bending pliers or other tools to provide the bone plate 100 with dorsal and/or other curvature, so as to conform the bone plate 100 to the features of a bone.

As explained in greater detail below, the bone plate 100 is configured to be secured to opposing bone portions of a bone discontinuity and to aid in compressing the bone portions together. To facilitate attachment to, and compression of, two or more bone portions, the bone plate 100 includes a plurality of through-holes or openings. The through-holes or openings are adapted to receive fasteners for securing the bone plate 100 to various bone portions of a bone discontinuity. Additionally, the through-holes or openings work cooperatively with fasteners and a compression clamp to allow compression of a bone discontinuity, as explained in greater detail below. Alternatively, or additionally, the through-holes or openings are adapted to alter the local rigidity of the bone plate 100, to permit the bone plate 100 to be manipulated with a tool (such as bending pliers), and/or to facilitate blood flow to a fracture or surgical site to promote healing.

The plurality of through-holes or openings can include one or more attachment holes. For example, FIG. 1A shows that the bone plate 100 includes three attachment holes 108. As shown by FIG. 1A, the attachment holes 108 are sized and configured to receive a K-wire or other similar guide wire. As explained in greater detail below, the attachment holes 108 are adapted to be used to temporarily secure the bone plate 100 to one or more bone portions in preparation of the placement of additional and/or more permanent fasteners.

In addition to attachment holes 108, the plurality of through-holes or openings can also include one or more fixation holes configured to receive one or more fixation fasteners that fix the bone plate to a bone, as explained in greater detail below. For example, FIG. 1A illustrates the bone plate 100 includes three fixation holes 110, 112, 114. One will appreciate in light of the disclosure herein that the fixation holes of the bone plates of the present invention may have any suitable position within the bone plate. For example, as shown in FIG. 1A, the fixation holes 110, 112, 114 are positioned in a line along the center portion of the bone plate 100. In alternative implementations, the fixation holes of the bone plate are arranged nonlinearly in a curved or staggered arrangement.

Additionally, in one or more implementations, the fixation holes 110, 112, 114 comprise threaded openings. In some implementations, the threads of the fixation holes 110, 112, 114 are configured to direct fixation fasteners inserted therein along non-parallel paths relative to the openings to help ensure that the fixation fasteners have adequate contact with the bone. Additionally or alternatively, the threads of the fixation holes 110, 112, 114 are configured to lock a fixation fastener inserted therein to the bone plate 100 and a portion of bone.

The bone plates of the present invention include one or more slide channels, e.g., an elongated slide channel. An elongated slide channel is any elongate opening having a length that is greater than its width. In some implementations, the length of the elongated slide channel is at least approximately twice the width of the elongated slide channel. In yet further implementations, the length of the elongated slide channel may be between approximately 2 and 20 times the width of the elongated slide channel. For example, FIG. 1A illustrates that the bone plate 100 has an elongated slide channel 116 with a length approximately 2.5 times the width thereof. As explained in greater detail below, the length of the elongated slide channel 116 determines the amount of compression provided by the bone plate 100. Thus, in one or more implementations the length of the elongated slide channel 116 is tailored based on the bone discontinuity with which the bone plate 100 is intended to be used.

As illustrated in implementation of FIG. 1A, the elongated slide channel 116 includes a counterbore 118 configured to receive, at least partially, a head of a fastener. In contrast to conventional compressions slots, in one or more implementation of the present invention the counterbore 118 is substantially uniform along its length. In other words, in one or more implementations, the counterbore 118 does not include a taper or incline that causes a screw head to move along the length of the elongated slide channel 116 as the screw is tightened.

The elongated slide channels of the present invention may have any suitable location along a bone plate. For example, as shown in the implementation of FIG. 1A, the elongated slide channel 116 is disposed near the center of the bone plate 100. Additionally, the elongated slide channels may be disposed between a pair of fixation holes. For example, FIG. 1A illustrates that the elongated slide channel 116 is disposed between a first fixation hole 110 and a second fixation hole 112. Alternatively, the elongated slide channel 116 may be disposed near an end of the bone plate (as defined by the length of the bone plate 100). For example, FIG. 2 illustrates a bone plate 200, including an elongated slide channel 216 located near an end of the bone plate 200.

One will appreciate as explained in greater detail below, that the elongated slide channel 116 and the fixation holes 110, 112, 114 work cooperatively to compress a bone discontinuity and fix the bone discontinuity in place. More specifically, a first reduction fastener is secured within a fixation hole 110, 112, 114 to a first bone portion, and a second reduction fastener is secured within the elongated slide channel 116 to a second bone portion. Using a compression clamp, the second reduction fastener and second bone portion are drawn along the elongated slide channel 116 toward the first reduction fastener and first bone portion to compress a bone discontinuity. In one or more implementations of the present invention, to aid in compressing a bone discontinuity, the elongated slide channel 116 is linearly aligned with at least one fixation hole. For example, FIG. 1A illustrates that the center of three fixation holes 110, 112, 114 are linearly aligned with the longitudinal axis 120 of the elongated slide channel 116. Alternatively, FIG. 2 illustrates that only a single fixation hole 214 is aligned with the elongated slide channel 216.

Additionally, while FIG. 1A illustrates a bone plate 100 with a single elongated slide channel 116, in alternative implementations; the bone plate includes two, three, four, or any suitable number of slide channels. For example, additional implementations of a bone plate include a pair of slide channels configured to act cooperatively with each other and/or fasteners placed therein for positioning the bone plate 100 in situ and compressing one or more bone discontinuities.

One will appreciate that the number and relative positioning of the slide channels can be based upon the type, number, and size of the bone discontinuities with which the bone plate is to be used. For example, FIG. 3 illustrates a bone plate 300 with a pair of elongated slide channels 316, 317 disposed substantially orthogonally to each other. One will appreciate that the bone plate 300 is adapted to compress two bone discontinuities. Additionally, the number and location of the fixation holes can also be varied depending upon the intended use of the bone plate. For example, FIG. 3 illustrates that the bone plate 300 includes four fixation holes 310, 311, 312, 314. First and second fixation holes 310, 311 are aligned with the first elongated slide channel 316, while third and fourth fixation holes 312, 314 are aligned with the second elongated slide channel 317.

In addition, or alternatively, to orthogonal orientation, elongated slide channels can also be positioned substantially parallel to each other or at any other orientation. For example, FIG. 4 illustrates a bone plate 400 having a first elongated slide channel 416 positioned in a substantially parallel orientation relative to a second elongated slide channel 417. Additionally, FIG. 4 illustrates that the bone plate 400 includes six fixation holes, with the first three fixation holes 410, 411, 412 being aligned with the first elongated slide channel 416, and the second three fixation holes 413, 414, 415 being aligned with the second elongated slide channel 417.

Figure 11:
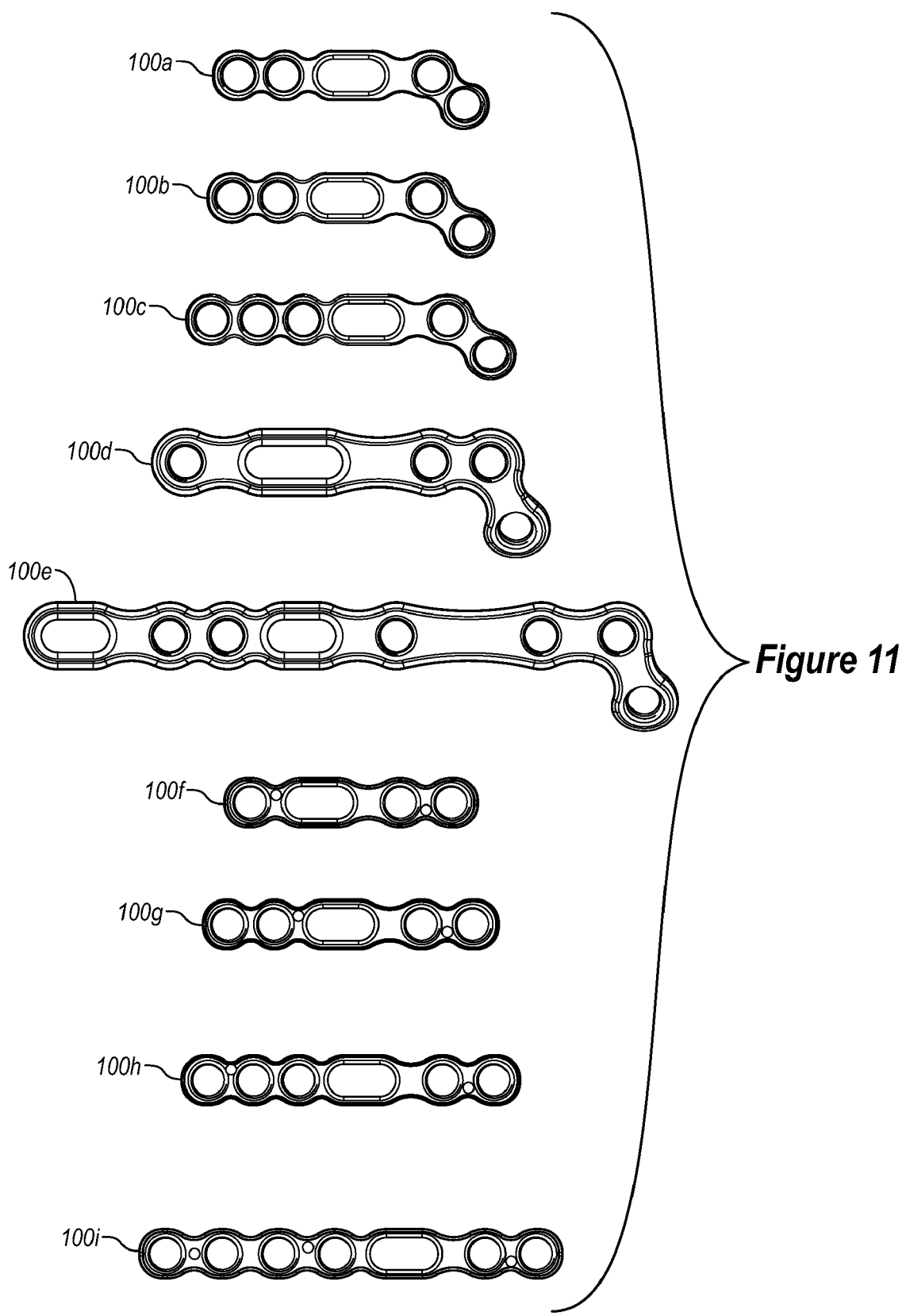
FIG. 11 illustrates additional implementations of various bone plates in accordance with implementations of the present invention.

In addition to the number and position of the elongated slide channels and the fixation holes, the bone plates of the present invention themselves can include a number of different configurations depending upon their intended use. For example, bone plates of the present invention include a linear shape (e.g., bone plate 100 of FIG. 1A), a Y-shape (e.g., bone plate 200 of FIG. 2), a T-shape (e.g., bone plate 300 of FIG. 3), a butterfly shape (e.g., bone plate 400 of FIG. 4), and other suitable shapes or configurations. Furthermore, FIG. 11 illustrates yet additional bone plates 11a-11i according to additional implementations of the present invention.

Additionally, the bone plates of one or more implementations of the present invention are configured to be used to correct bone discontinuities in or between the smaller bones of the foot or hand, such as for example, metatarsophalangeal joint fusions, lapidus procedures, or metatarsal fractures. One will appreciate, however, that the bone plates of other implementations of the present invention are configured to be used to repair any number and type of bone discontinuity. For example, the bone plates of various implementations of the present invention are configured for use on or between any suitable bones of the human body and/or other vertebrate species. Exemplary bones include bones of the arms (radius, ulna, humerus), legs (femur, tibia, fibula, patella), hands, feet, the vertebrae, scapulas, pelvic bones, cranial bones, ribs, clavicles, etc. Depending on the type of bones and type of bone discontinuities, the size and shape of the bone plate, number and position of fixation holes, and number and position of elongated slide channels vary.

As mentioned previously, in addition to a bone plate, kits of the present invention include one or more fasteners that work in conjunction with the bone plate. For example, FIG. 5 illustrates a side perspective view of an exemplary reduction fastener 500 according to an implementation of the present invention. As explained in greater detail below, the reduction fastener 500 is configured to both secure a bone plate 100, 200, 300, 400 to a portion of a bone discontinuity, and also aid in compressing bone portions of a bone discontinuity. In the illustrated implementation, the reduction fastener 500 comprises a head 510, a shaft 512, and a tip 514.

As FIG. 5 shows, the head 510 includes a recess 502 configured to receive a portion of a rotational tool, such as, for example, a drill or screw driver. More specifically, the recess comprises a void into which a portion of a rotation tool can be inserted. One will appreciate that the rotational tool may provide the force necessary to rotate the reduction fastener 500 into a portion of bone or other material. FIG. 5 illustrates that the recess 502 comprises a hexagon shape. When a rotation tool is inserted into the recess 502 and rotated, the rotational tool engages the lateral surfaces of the recess 502 in a manner so as to provide sufficient rotational torque to rotate the reduction fastener 500.

As will be appreciated by those skilled in the art, the recess 502 can comprise a variety of different types and configurations without departing from the scope and spirit of the present invention. For example, in one implementation, the recess 502 comprises a flattened slot. In yet another implementation, the recess 502 comprises a slot having a crossing pattern.

The head 510 of the reduction fastener 500 also comprises one or more engagement features that allow it (and a portion of bone secured to the reduction fastener 500) to be pulled along an elongated slide channel of a bone plate, thereby compressing a bone discontinuity. More specifically, the head 510 of the reduction fastener 500 comprises one or more engagement features configured to be engaged by a compression clamp (see FIG. 8), which a practitioner may use to draw two reduction fasteners 500 together. For example, FIG. 5 illustrates that the head 510 includes an annular engagement groove 518 extending radially therein. The annular engagement groove 518 exposes a neck 520 of reduced diameter, which is adapted to be engaged by a compression clamp.

As will be appreciated by those skilled in the art, engagement features of the head 510 are not limited to annular engagement grooves 510; thus, alternative implementations include a variety of types and configurations of engagement features. For example, in an alternative implementation, the head 510 of the reduction fastener 500 can include an engagement slot (not shown). The engagement slot comprises a hole extending through the head 510 of the reduction fastener 500, which is adapted to receive a portion of a compression clamp. In yet a further implementation of the present invention, the recess 502 of the head 510 comprises an engagement feature configured to be used in combination with a compression clamp.

In addition to an annular engagement groove 518 and the recess 502, the head 510 of the reduction fastener includes a shoulder. For example, FIG. 5 illustrates that the head 510 comprises a rounded shoulder 516 that tapers along its length towards the shaft 512. The rounded shoulder 516 is configured to mate with the counterbore 118 (FIG. 1A) of an elongated slide channel 116 of a bone plate 100. More particularly, the rounded shoulder 516 is configured to allow the reduction fastener 500 to be pulled along the counterbore 118 (FIG. 1A) of an elongated slide channel 116.

As a fastener, the reduction fastener 500 includes threads that facilitate advancement of reduction fastener 500 into, and secures the reduction fastener 500 to, bone, tissue, or other material. For example, FIG. 5 illustrates that the shaft 512 of the reduction fastener 500 includes a single thread 522 that forms a spiral pattern extending from the head 510 to the tip 514 of the reduction fastener 500. In alternative implementations the shaft 512 includes a plurality of threads 522. In any event, the threads 522 are configured to engage bone, tissue, or other material and help the reduction fastener 500 advance therein.

In one or more implementations of the present invention, the reduction fastener 500 is self-starting and self-tapping. For example, FIG. 5 illustrates that the tip 514 of the reduction fastener 500 includes one or more flutes or teeth 524. The flutes 524 extend at least partially along the shaft 512, thereby dividing the proximal threads 522 of the shaft 512 into two or more sections. One will appreciate that the threads 522 are configured to be utilized with the flutes 524 to facilitate self-tapping of the reduction fastener 500 into the material into which it is to be inserted. For example, the flutes 524 are configured to cut a path into which the threads 522 follow.

In some implementations the reduction fastener 500 can include a partial or full cannula. The cannula can comprise a channel extending from tip 514 to head 510 along the length of the reduction fastener 500. The cannula can accommodate a thread, suture, guidewire or similar filament or other member permitting a practitioner to insert reduction fastener 500 to a desired position in a patient.

Figure 6:
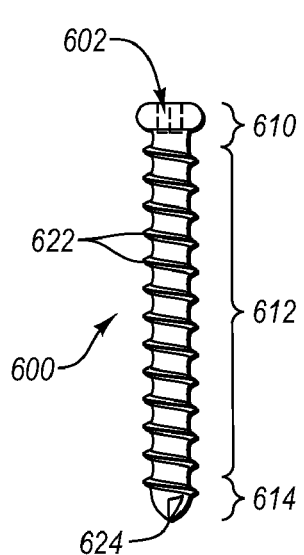
FIG. 6 illustrates a side perspective-view of a fixation fastener in accordance with an implementation of the present invention.

In addition to reduction fasteners 500, one or more implementations of a kit of the present invention may also include one or more fixation fasteners. The fixation fasteners may generally comprise any mechanism for affixing a bone plate to a bone, including screws, pins, and wires, among others. As shown in FIG. 6, in one implementation the fixation fastener comprises a bone screw 600. For example, FIG. 6 illustrates an exemplary fixation fastener 600, including a head 610, a shaft 612 with threads 622 extending along at least a portion thereof, and a tip 614.

In some implementations, the fixation fastener 600 is configured as a unicortical or bicortical bone screw, and thus, has relatively small threads 622 for use in hard bone, such as typically found in the shaft portion of a bone. In alternative implementations, the fixation fastener 600 is configured as a cancellous bone screws and has relatively larger threads for use in soft bone, such as typically found near the ends (periarticular regions) of a bone.

As a fastener, the threads 622 of the fixation fastener 600 facilitate advancement of fixation fastener 600 into, and secure the fixation fastener 600 to, bone, tissue, or other material. For example, FIG. 6 illustrates that the shaft 612 of the fixation fastener 600 includes a single thread 622 that forms a spiral pattern extending from the head 610 to the tip 614 of the fixation fastener 600. In alternative implementations the shaft 612 includes a plurality of threads 622. In any event, the threads 622 engage bone, tissue, or other material and help the fixation fastener 600 advance therein.

While FIG. 6 shows the thread 622 of the fixation fastener 600 extending along the entire length of the shaft 612, the present invention is not so limited. As such, in alternative implementations, the threads 622 extend along only a portion of the length of the shaft 612. For example, in some implementations the shaft 612 includes an un-threaded portion proximate the head 610.

In one or more implementations of the present invention, the fixation fastener 600 is self-starting and self-tapping. For example, FIG. 6 illustrates that the tip 614 of the reduction fastener 600 includes one or more flutes or teeth 624. The flutes 624 extend at least partially along the shaft 612, thereby dividing the proximal threads 622 of the shaft 612 into two or more sections. One will appreciate that the threads 622 are configured to be utilized with the flutes 624 to facilitate self-tapping of the reduction fastener 600 into the material into which it is to be inserted.

Furthermore, as FIG. 6 shows, the head 610 includes a recess 602 configured to receive a portion of a rotational tool, such as, for example, a drill or screw driver. More specifically, the recess 602 comprises a void into which a portion of a rotation tool can be inserted. One will appreciate that the rotational tool may provide the force necessary to rotate the fixation fastener 600 into a portion of bone or other material. As will be appreciated by those skilled in the art, the recess 602 can comprise a variety of types and configurations, such as those described above with relation to the recess 502 of the reduction fastener 500, without departing from the scope and spirit of the present invention.

Additionally, similar to the reduction fastener 500, in some implementations the fixation fastener 600 can include a partial or full cannula. The cannula can comprise a channel extending from tip 614 to head 610 along the length of the fixation fastener 600. The cannula can accommodate a thread, suture, guidewire or similar filament or other member permitting a practitioner to insert reduction fastener 600 to a desired position in a patient.

As explained in greater detail below, the fixation fastener 600 is configured to be inserted within a fixation hole 110, 112, 114 and/or an elongated slide channel 116 of a bone plate 100 to facilitate securement of the bone plate 100 to a portion of bone. Furthermore, in one or more implementations, the fixation fastener 600 is configured to lock into a fixation hole 110, 112, 114 of a bone plate 100. For example, the threads 622 of the fixation fastener 600 are configured to lock into the threads of a fixation hole 110, 112, 114.

Figure 7:
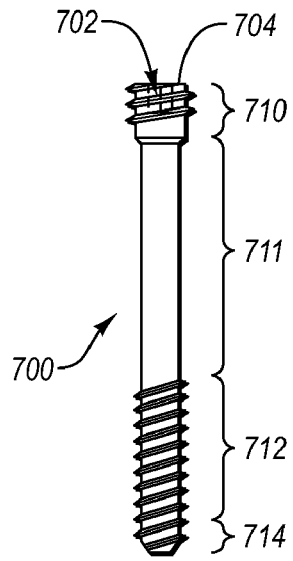
FIG. 7 illustrates a side perspective-view of a compression fastener in accordance with an implementation of the present invention.

In addition to the fasteners described herein above for use in combination with a bone plate, one or more implementations of a kit of the present invention includes one or more additional fasteners for providing additional compression of a bone discontinuity separately from a bone plate. For example, FIG. 7 illustrates a side perspective-view of an exemplary compression fastener 700. As shown in FIG. 7, the compression fastener 700 is headless. The headless configuration of the compression fastener 700 allows for distal end 704 of the compression fastener 700 to be placed in a substantially flush configuration with the outer surface of a bone into which the compression fastener 700 is inserted. Thus, the headless configuration of the compression fastener 700 reduces discomfort for the patient.

As shown by FIG. 7, the compression fastener 700 comprises a distal threaded portion 710, an un-threaded portion 711, a proximal threaded portion 712, and a tip 714. To aid in generating compression, the proximal thread portion 712 of the compression fastener 700 are configured to advance faster than distal threaded portion 710, thereby allowing for compression of a bone discontinuity along the un-threaded portion 711 of the compression fastener 700. For example, in one or more implementations of the present invention, the pitch of the threads of the distal threaded portion 710 are smaller than the pitch of the threads of the proximal threaded portion 712, thereby causing the proximal threaded portion 712 to advance quicker than the distal threaded portion 710. In addition, or alternatively, the angle of the threads of the proximal threaded portion 712 is greater than the angle of the threads of the distal threaded portion 710, thereby causing the proximal threaded portion 712 to advance quicker than the distal threaded portion 710.

Furthermore, as FIG. 7 shows, the distal end 704 of the compression fastener 700 includes a recess 702 configured to receive a portion of a rotational tool, similar to the recesses 502 and 602 described herein above in relation to the reduction fastener 500 (FIG. 5) and the fixation fastener 600 (FIG. 6). Additionally, in some implementations the compression fastener 700 can include a partial or full cannula. The cannula can comprise a channel extending from tip 714 to the distal end 704 along the length of the compression fastener 700. The cannula can accommodate a thread, suture, guidewire or similar filament or other member permitting a practitioner to insert compression fastener 700 to a desired position in a patient.

Figure 8A:
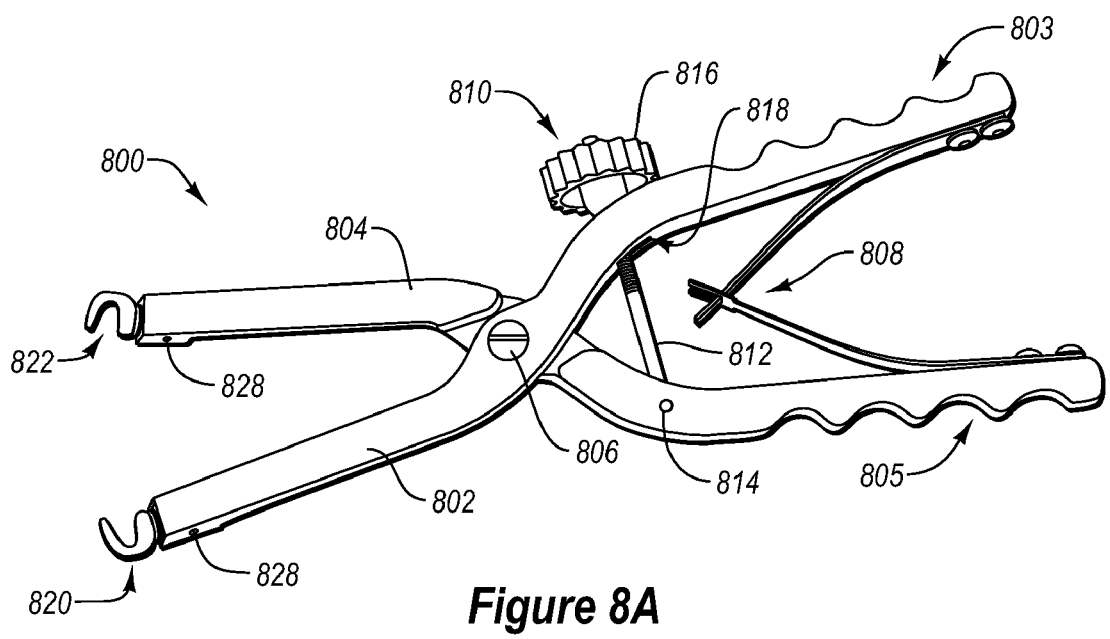
FIG. 8A illustrates a top perspective-view of a compression clamp in accordance with an implementation of the present invention.
Figure 8B:
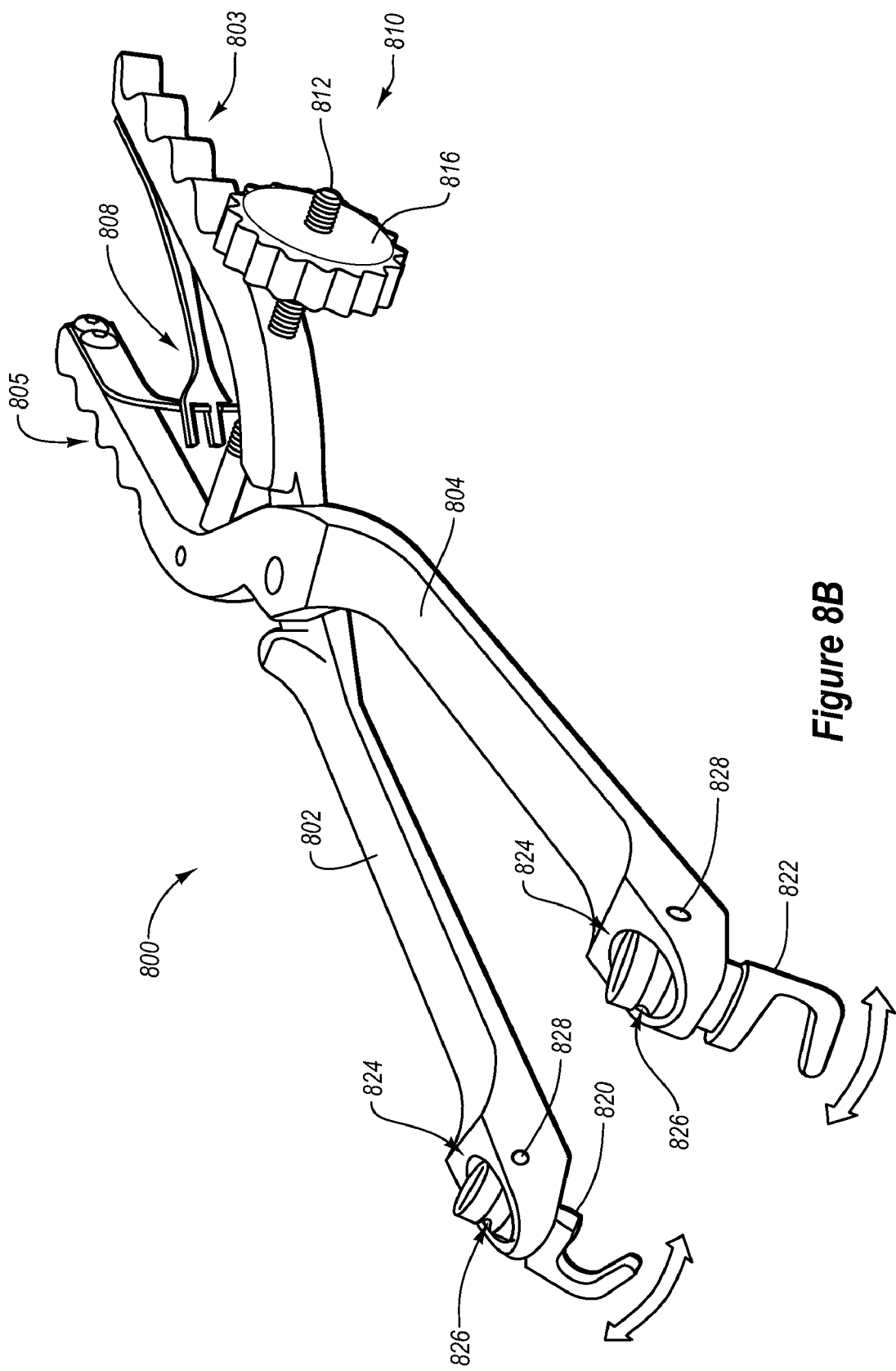
FIG. 8B illustrates a bottom perspective-view of the compression clamp of FIG. 8A.

Referring now to FIGS. 8A-8B, an exemplary compression clamp 800 of a kit of one or more implementations of the present invention is illustrated. As shown by FIG. 8A, the compression clamp 800 comprises a first lever 802 secured to a second lever 804 via a pivot 806. Each of the levers 802 includes a first end having a handle 803, 805, and a second end having an engagement member 820, 822. Furthermore, the compression clamp 800 include a biasing mechanism 808 configured to bias the ends of the first lever 802 away from the ends of the second lever 804. Thus, to close the compression clamp 800, or in other words draw the first engagement members 820, 822 toward each other, a user squeezes the handles 803, 805 of the first and second levers 802, 804 together.

The compression clamp 800 further includes a locking mechanism 810 configured to lock the positions of the engagement members 820, 822 relative to each other in one or more directions. For example, FIG. 8 illustrates that one implementation of a locking mechanism 810 of a compression clamp 800 includes a threaded rod 812 and a lock nut 816. More specifically, FIG. 8 illustrates that the threaded rod 812 is secured to the second lever 804 via a pivot 814, and extends through a slot 818 in the first lever 802. To lock the compression clamp 800, a practitioner translates the lock nut 816 along the threaded rod 812 until it engages the first lever 802, thereby preventing the compression clamp 800 from opening.

As mentioned previously, the compression clamp 800 includes a pair of engagement members 820, 822 configured to engage a head 510 of a reduction fastener 500 (FIG. 5). For example, FIG. 8 illustrates that in at least one implementation, the engagement members 820, 822 comprise hooks. The hooks 820, 822 are sized and configured to be inserted within an engagement groove 518 and around a neck 520 of a reduction fastener 500 (FIG. 5). In alternative implementations, the engagement members 820, 822 comprise rods sized and configured to be inserted within an engagement slot formed within the head 510 of a reduction fastener 500, or within a recess 502 of a reduction fastener 500.

In any event, in at least one implementation of the present invention, the engagement members 820, 822 are pivotally secured to the levers 802, 804 of the compression clamp 800. For example, FIG. 8B illustrates that the engagement members 820, 822 are secured within a respective hole 824 in the respective levers 802, 804. Thus, the engagement members 820, 822 are adapted to swivel or pivot within the holes 824 relative to the compression clamp 800, as illustrated by the arrows in FIG. 8B.

Furthermore, in some implementations of the present invention, the engagement members 820, 822 are configured to pivot within a limited range of motion. For example, FIG. 8B illustrates that each engagement members 820, 822 includes a first channel 826 extending into a first side thereof. Additionally, each engagement member 820, 822 includes a second channel (not shown) extending into an opposing side thereof. Furthermore, each lever 802, 804 includes a pivot pin 828 extending within the second channel. The second channel provides each engagement member 820, 822 with a limited range of pivoting motion. In particular, as an engagement member 820, 822 is pivoted within hole 824 in a first direction, one side of the second channel will eventually engage the pivot pin 828, thereby preventing further pivoting in the first direction. Similarly, as an engagement member 820, 822 is pivoted within hole 824 in a second direction, an opposing side of the second channel will eventually engage the pivot pin 828, thereby preventing further pivoting in the second direction.

One will appreciate that the amount of pivoting motion of the engagement members 820, 822 is dictated by the depth that the second channel extends into and around the engagement members 820, 822. The more the second channel extends around and into the engagement member 820, the greater the range of motion allowed before the second channel engages the pivot pin 828. In some implementations of the present invention, the engagement members 820, 822 are allowed to swivel or pivot within the holes 824 up to approximately ninety degrees. In additional implementations of the present invention, the engagement members 820, 822 are allowed to swivel or pivot within the holes 824 between an approximately five degree range and an approximately thirty-degree range of motion. In further implementations of the present invention, the engagement members 820, 822 are allowed to swivel or pivot within the holes 824 through an approximately fifteen-degree range of motion.

The pivotal connection to the levers 802, 804 allows the engagement members 820, 822 to pivot relative to the compression clamp 800, about the head 510 of the reduction fastener 500. One will appreciate in light of the disclosure herein that the pivoting of the engagement members 820, 822 allows for compensation of height, angle, and other various misalignments of the reduction fasteners 500 due to complications inherent in surgery, difference in surface contours of the bone portions of a bone discontinuity, or other real world circumstances. The limited range of motion provided to the engagement members 820, 822 ensures that engagement members 820, 822 do not pivot or swivel so much as to prevent or delay engagement with a reduction fastener 500 by becoming an additional source of misalignment.

In one or more implementations of the present invention, the surgical components described herein above are provided as a kit for use to repairing bone. One will appreciate that such a kit may include other conventional medical instruments, such as, for example, a scalpel, a saw, a drill and/or a screw-driver. The use of these elements in an exemplary surgical operation will now be described with reference to FIGS. 9-10F, which illustrate the repair of an exemplary bone discontinuity.

Referring now to FIG. 9, an exemplary bone discontinuity, which a kit of the present invention may be used to correct, is shown. More specifically, FIG. 9 illustrates a dislocation 900 of the first metatarsophalangeal joint, or in other words, a dislocation of the first metatarsal bone 902 and the first proximal phalange 904. While the exemplary method described herein is in relation to the correction of a first metatarsophalangeal joint dislocation 900, one will appreciate that this is just one exemplary bone discontinuity that the kit, components, and methods of the present invention may be used to correct.

Indeed, by varying the type, shape, and number of bone plates, reduction fasteners, fixation fasteners, and/or compression fasteners, kits and components of the present invention can correct most, if not all, types of bone discontinuities. As used herein the term "bone discontinuity" refers to any separation of bone portions, whether the bone portions are separate bones or portions of the same bone. Furthermore, as used the term "bone portion" refers to both natural and artificial bone, such as implants. Thus, implementations of the present invention can be used to fuse bones together, correct fractures or clean breaks, graft segments of bone together, or otherwise draw two bone portions together.

The first step in one implementation of a method of the present invention includes prepping the bone discontinuity 900. In particular, a practitioner exposes the bone discontinuity. Depending on the type of bone discontinuity, prepping the bone discontinuity 900 further involves de-articulation between bones to be fused. For example, in the specific example of a dislocation 900 of the first metatarsophalangeal joint, prepping the bone discontinuity 900 involves de-articulation of the joint between the first metatarsal bone 902 and the first proximal phalange 904.

After prepping the bone discontinuity 900, or alternatively, prior to or in conjunction therewith, the practitioner selects a bone plate. For example, the type, shape of bone plate (e.g., linear, Y-shaped, T-shaped, butterfly shaped), length, and thickness of bone plate is selected based on the particular bone discontinuity. For example, FIG. 10A illustrates that a practitioner selects a linear bone plate 100 for use with the dislocation 900 of the first metatarsophalangeal joint.

In conjunction with selecting the bone plate 100, a practitioner may also contour, or otherwise shape, the bone plate 100 to correspond with the bone discontinuity 900 being corrected. For example, the practitioner may add dorsal curvature to the bone plate 100 by using a pair of bending pliers.

The method then involves placing the bone plate 100 adjacent the bone discontinuity 900. For example, FIG. 10A illustrates that a practitioner spans the bone plate 100 across the bone discontinuity 900. More specifically, the practitioner ensures that the elongated slide channel 116 extends over and across the bone discontinuity 900. Additionally, the practitioner ensures that at least one fixation hole 114, 112 is positioned above a first portion 902 of the bone discontinuity 900, and at least a second fixation hole 110 is positioned above a second portion 904 of the bone discontinuity 900.

Optionally, the method can include temporarily fixing the bone plate 100 about the bone discontinuity 900. For example, a practitioner secures the bone plate 100 to the bone discontinuity 900 by via a guide wire or K-wire through one or more of the attachment holes 108 of the bone plate 100 to the first portion 902 and/or the second portion 904 of the bone discontinuity 900.

Referring now to FIG. 10B, the method involves securing a first reduction fastener 500a within a first fixation hole 114 of the bone plate 100 and to the first bone portion 902. One will appreciate that the first reduction fastener 500a can be secured to the first bone portion 902 in any number of ways. For example, in one implementation, a practitioner drills a pilot hole into the first bone portion 902, and then tightens the first reduction fastener 500a into the pilot hole of the first bone portion 902. Additionally or alternatively, when the first reduction fastener 500a comprises a cannula, the practitioner first places a guidewire within the first fixation hole 114 and into the first bone portion 902, and then tracks the first reduction fastener 500a along the guidewire and into the first bone portion 902. In yet further implementations, when the first reduction fastener 500a is self-tapping, the practitioner secures the reduction fastener 500a directly into the first bone portion 902 without the use of pilot hole or guidewire.

Along similar lines, the method also involves securing a second reduction fastener 500b within the elongated slide channel 116 of the bone plate 100 and to the second bone portion 904. One will appreciate that the second reduction fastener 500b can be secured to the second bone portion 904 in any of the ways described above with reference to securing the first reduction fastener 500*a* to the first bone portion 902.

The method optionally further involves securing a first fixation fastener 600*a* within a second fixation hole 112 of the bone plate 100 and to the first bone portion 902. One will appreciate that the first fixation fastener 600*a* can be secured to the first bone portion 902 in any number of ways. For example, in one implementation, a practitioner drills a pilot hole into the first bone portion 902, and then tightens the first fixation fastener 600*a* into the pilot hole of the first bone portion 902. Additionally or alternatively, when the first fixation fastener 600*a* comprises a cannula, the practitioner first places a guidewire within the second fixation hole 112 and into the first bone portion 902, and then tracks the first fixation fastener 600*a* along the guidewire and into the first bone portion 902. In yet further implementations, when the first fixation fastener 600*a* is self-tapping, the practitioner secures it directly into the fi portion 902 without the use of pilot hole or guidewire.

Additionally, securing the fixation fastener 600*a* to the first bone portion 902 can optionally comprise angling the first fixation fastener 600*a* relative to the bone plate 100. For example, the practitioner angles the first fixation fastener 600*a* away from the bone discontinuity 900 or otherwise helps ensure that the first fixation fastener 600*a* is securely fastened to the first bone portion 902.

Figures 10C, 10D:
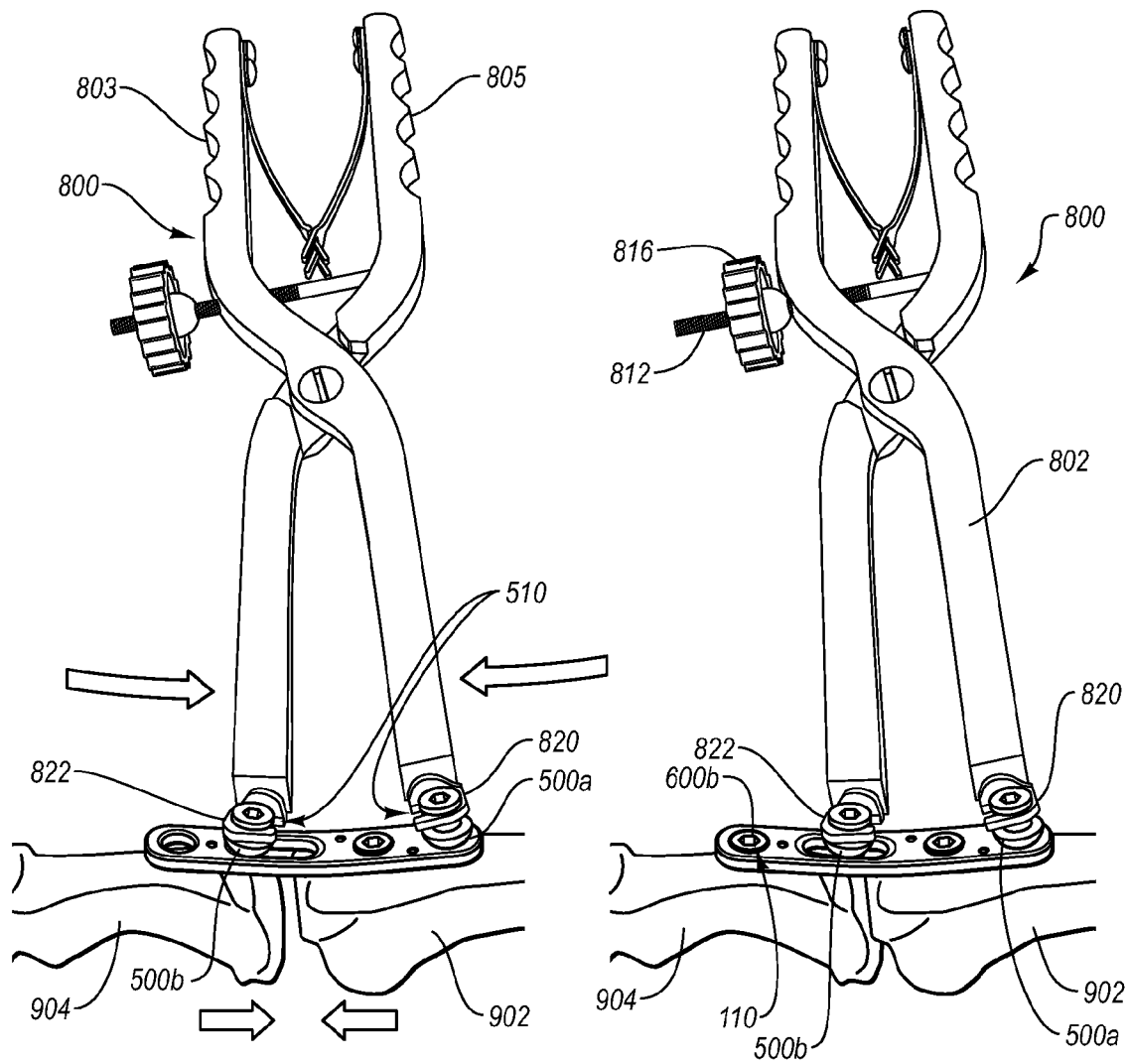
FIG. 10C illustrates the compression clamp of FIGS. 8A-8B placed about the reduction fasteners of FIG. 10B.
FIG. 10D illustrates the compression clamp of FIG. 10C in a locked configuration after the reduction fasteners of FIG. 10B have been compressed together to reduce the exemplary bone discontinuity.

As shown in FIG. 10C, one will appreciate that an implementation of a kit of the present invention includes a bone plate 100, a pair of reduction fasteners 500*a*, 500*b*, at least one fixation fastener 600*a*, and a compression clamp 800. As shown in FIG. 10C, the method further involves using the kit to compress the bone discontinuity 900. In particular, the method involves engaging the first and second reduction fasteners 500*a*, 500*b* with the compression clamp 800. Specifically, the practitioner positions a first engagement member 820 of the compression clamp 800 about the head 510 of the first reduction fastener 500*a*, and a second engagement member 822 of the compression clamp 800 about the head 510 of the second reduction fastener 500*b*. In at least one implementation of the present invention, positioning an engagement member 820, 822 about the head 510 of a reduction fastener 500 involves causing the engagement member 820, 822 to pivot relative to the compression clamp 800 and about the head 510 of the reduction fastener 500. One will appreciate in light of the disclosure herein that the pivoting of the engagement member 820, 822 can compensate for height, angle, and other various misalignments of the reduction fastener 500 due to complications inherent in surgery, difference in surface contours of the bone portions 902, 904, or other real world circumstances.

Alternatively, positioning the engagement members 820, 822 of the compression clamp 800 about the heads 510 of the reduction fasteners 500*a*, 500*b* involves inserting a hook 820 within an engagement groove 518 of reduction fastener 500 and about the neck 520 of the head 510 of the reduction fastener 500. In yet further implementations, the method can involve positioning an engagement rod within an engagement slot of the head 510 of the reduction fastener 500.

After having secured the engagement members 820, 822 of the compression clamp 800 about the reduction fasteners 500*a*, 500*b*, the method involves closing the compression clamp 800 thereby drawing the second reduction fastener 500*b* (and the second bone portion 904) along the elongated slide channel 116 toward the first reduction fastener 500*a* (and the first bone portion 902), thereby compressing the bone discontinuity 900. To close the compression clamp 800, the practitioner squeezes the handles 803, 805 together, thereby drawing the first engagement member 820 toward the second engagement member 822, as illustrated by the arrows in FIG. 10C. One will appreciate in light of the disclosure herein that compressing the bone discontinuity 900 by physically closing the compression clamp 800, the practitioner has the ability to manually control the amount of compression and/or manually adjust the osteotomy before final fixation of the bone plate 100.

As mentioned previously, the kit can thus allow a practitioner to not only manually control the compression and reduction of a bone discontinuity 900, but to also feel and/or see the amount of compression. The ability to feel and/or see the amount of compression allows the practitioner to properly set the spacing and alignment between bone portions 902, 904 of the bone discontinuity 900, and thereby help ensure proper healing. In other words, one or more implementations of a kit of the present invention provide a practitioner with physical or tactile feedback during the compression of the bone discontinuity 900, and thus, provide the practitioner with the ability to better control the compression and spacing of bone portions 902, 904 during a reduction.

After compressing the first bone portion 902 and the second bone portion 904 together as desired, the practitioner then locks the compression clamp 800. For example, FIG. 10D illustrates that the practitioner tightens the lock nut 816 against the first lever 802 of the compression clamp 800 by translating the lock nut 816 along the threaded rod 812. One will appreciate in light of the disclosure herein that locking the compression clamp 800 includes locking the position of the first engagement member 820, and thus the first reduction fastener 500*a* and first bone portion 902, relative to the second engagement member 822, and thus the second reduction fastener 500*b* and the second bone portion 904.

After locking the bone portions 902, 904 relative to each other, the practitioner secures a second fixation fastener 600*b* within a third fixation hole 110 of the bone plate 100 and to the second bone portion 904. One will appreciate that the second fixation fastener 600*b* can be secured to the second bone portion 904 in any of the ways described above with reference to securing the first fixation fastener 600*a* to the first bone portion 902.

Figure 10E:
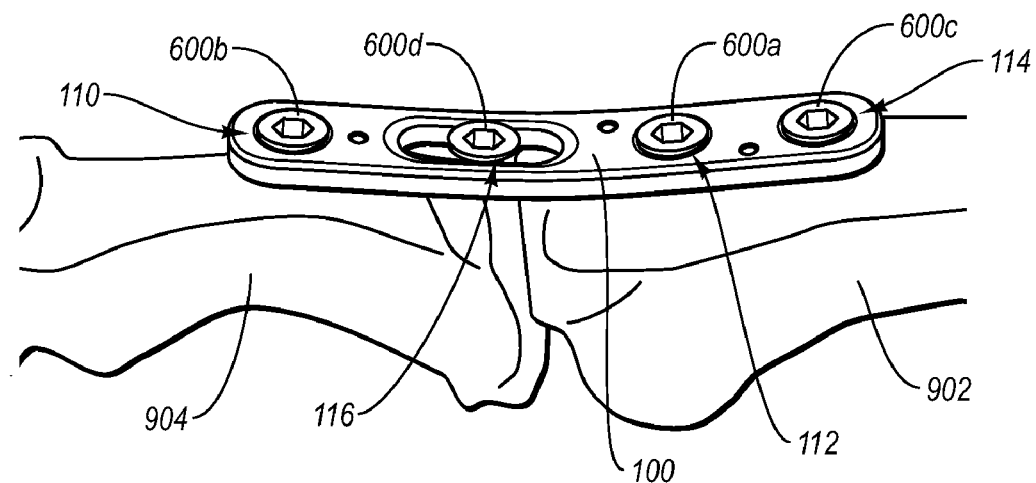
FIG. 10E illustrates the bone plate of FIG. 10A secured to the bone portions of the exemplary bone discontinuity, which have been aligned and compressed together.

With both the first and second fixation fasteners 600*a*, 600*b* secured within the fixation holes 110, 112 of the bone plate 100, and to the opposing bone portions 902, 904 of the bone discontinuity 900, the practitioner removes the compression clamp 800 and the first and second reduction screws 500*a*, 500*b*. Then as shown by FIG. 10E, the practitioner can optionally secure a third fixation fastener 600*c* within the first fixation hole 114 to the first bone portion 902 to provide additional fixation. Furthermore, the practitioner can also optionally insert a fourth fixation fastener 600*d* with the elongated slide channel 116 and to the second bone portion 904 to provide yet additional fixation of the bone discontinuity 900. One will appreciate that the third and fourth fixation fasteners 600*c*, 600*d* are inserted within the holes formed in the first and second bone portions 902, 904 formed by inserting the first and second reduction fasteners 500*a*, 500*b* repetitively therein.

Figure 10F:
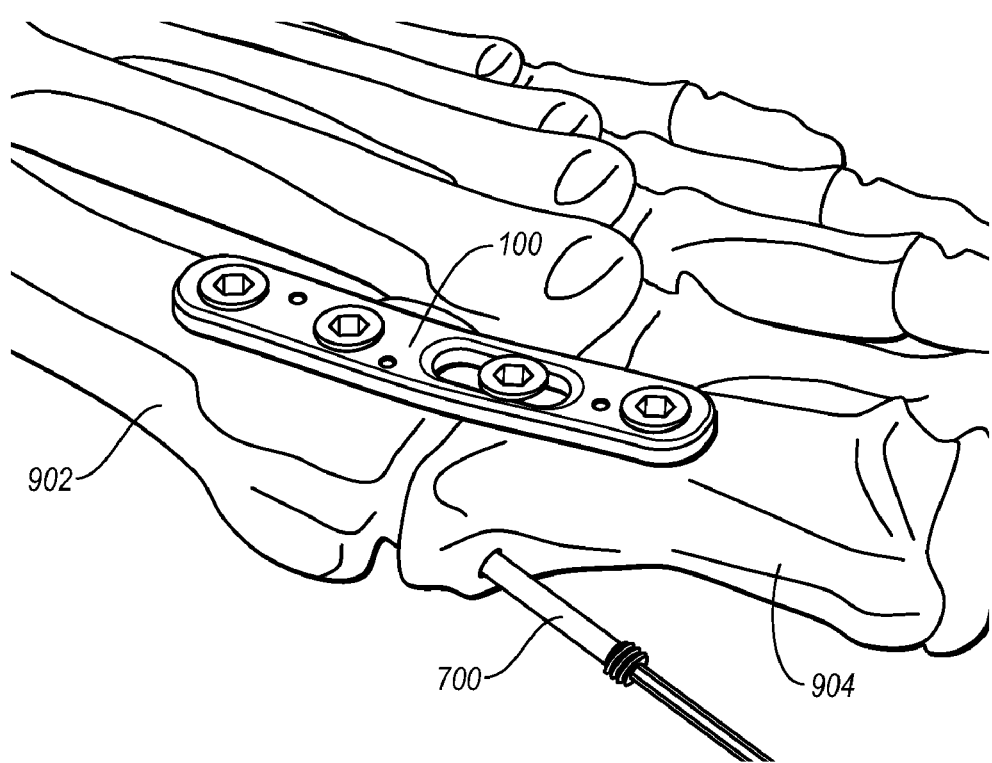
FIG. 10F illustrates a view of the compression fastener of FIG. 7 being inserted about the reduced exemplary bone discontinuity.

After having secured the bone plate 100 to the opposing bone portions 902, 904 of the bone discontinuity 900 via two or more fixation screws 600, the practitioner can optionally provide even further fixation to the bone discontinuity 900 by adding one or more additional fixation devices. For example, FIG. 10F illustrates that the practitioner secures compression fastener 700 into the first and second bone portions 902, 904 of the bone discontinuity 900.

Accordingly, one or more implementations of components, a kit, and methods described herein provide a practitioner with a great deal of functional versatility in repairing bone discontinuities. Furthermore, as discussed herein, the components, kit, and methods of one or more implementations of the present invention allow for efficient and accurate correction of various different types of bone injury by allowing a practitioner to manually control the compression and reduction of a bone discontinuity, while receiving physical feedback on amount of compression.

One will appreciate in light of the disclosure herein that the present invention may be embodied in other specific forms without departing from its spirit or essential characteristics. In addition, the structures and processes described herein can be deviated in any number of ways within the context of implementations of the present invention. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

I claim:

1. A method of surgically repairing bone, comprising:
   temporarily securing a bone plate to one or more of a first bone portion and a second bone portion using one or more wires;
   securing a first reduction fastener within a first fixation hole of said bone plate and to the first bone portion;
   securing a second reduction fastener within an elongated slide channel of said bone plate and to the second bone portion;
   positioning a first engagement member of a compression clamp about a head of said first reduction fastener;
   positioning a second engagement member of said compression clamp about a head of said second reduction fastener;
   closing said compression clamp thereby drawing said second reduction fastener and the second bone portion along said elongated slide channel toward said first reduction fastener and the first bone portion; and
   securing a fixation fastener within a second fixation hole of said bone plate and to the second bone portion, and further comprising:
   removing said first reduction fastener and said second reduction fastener from said bone plate; and
   securing an additional fixation fastener within said first fixation hole and to the first bone portion.

2. The method of claim 1, further comprising locking the position of said first engagement member relative to said second engagement member.

3. The method of claim 1, wherein positioning said first engagement member about said head of said first reduction fastener comprises causing said first engagement member to pivot relative to said compression clamp.

4. The method of claim 1, further comprising securing a third fixation fastener within a third fixation hole of said bone plate and to the first bone portion.

5. The method of claim 1, wherein closing the compression clamp comprises manually squeezing together handles of the compression clamp.

6. A method of surgically repairing bone, comprising:
   placing a bone plate across a bone discontinuity, wherein the bone discontinuity comprises one of a bone joint or a bone fracture;
   securing a first reduction fastener within a first fixation hole of a bone plate and to a first bone portion;
   securing a second reduction fastener within an elongated slide channel of the bone plate and to a second bone portion;
   positioning a first engagement member of a compression clamp about an exterior surface of the first reduction fastener;
   positioning a second engagement member of the compression clamp about an exterior surface of the second reduction fastener;
   closing the compression clamp by manually squeezing together handles of the compression clamp, thereby drawing the second reduction fastener and the second bone portion along the elongated slide channel toward the first reduction fastener and the first bone portion; and
   securing a fixation fastener within a second fixation hole of the bone plate and to the second bone portion.

7. The method of claim 6, further comprising removing the first reduction fastener and the second reduction fastener from the bone plate; and
   securing an additional fixation fastener within the first fixation hole and to the first bone portion.

8. The method of claim 6, wherein positioning the first engagement member about an exterior surface of the first reduction fastener comprises causing the first engagement member to pivot relative to the compression clamp.

9. The method of claim 6, further comprising securing a third fixation fastener within a fixation hole of the bone plate and to the first bone portion.

10. The method of claim 6, further comprising temporarily securing the bone plate to one or more of the first bone portion and the second bone portion by inserting one or more wires through one or more attachment holes in the bone plate and into one or more of the first bone portion and the second bone portion.

11. The method as recited in claim 6, wherein positioning the first engagement member about an exterior surface of the first reduction fastener comprises positioning the first engagement member about a neck of the first reduction fastener.

12. The method as recited in claim 6, wherein the first and second reduction fasteners comprise screws.

13. The method as recited in claim 6, wherein the first and second reduction fasteners comprise wires.

14. The method as recited in claim 6, further comprising locking the compression clamp, thereby locking a position of the second bone portion relative to the first bone portion.

15. The method as recited in claim 6, wherein positioning the first engagement member of the compression clamp about the exterior surface of the first reduction fastener comprises positioning a first hook at least partially about a portion of a first engagement feature of the first reduction fastener that is positioned above the bone plate.

16. The method as recited in claim 15, wherein positioning the second engagement member of the compression clamp about the exterior surface of the second reduction fastener comprises positioning a second hook at least partially about a portion of a second engagement feature of the second reduction fastener that is positioned above the bone plate.

17. The method as recited in claim 6, wherein securing the second reduction fastener within the elongated slide channel of the bone plate and to the second bone portion comprises advancing the second reduction fastener until a rounded shoulder of the second reduction fastener engages the elongated slide channel.

18. A method of surgically repairing bone, comprising:

placing a bone plate across a bone discontinuity, wherein the bone discontinuity comprises one of a bone joint or a bone fracture;

securing a first reduction fastener within a first fixation hole of a bone plate and to a first bone portion such that a first engagement feature of the first reduction fastener is positioned above the bone plate;

securing a second reduction fastener within an elongated slide channel of the bone plate and to a second bone portion such that a second engagement feature of the second reduction fastener is positioned above the bone plate;

engaging a first engagement member of a compression clamp with the first engagement feature of the first reduction fastener;

engaging a second engagement member of the compression clamp with the second engagement feature of the second reduction fastener;

closing the compression clamp by manually squeezing together handles of the compression clamp, thereby drawing the second reduction fastener and the second bone portion along the elongated slide channel toward the first reduction fastener and the first bone portion; and securing a fixation fastener within a second fixation hole of the bone plate and to the second bone portion.

19. The method of claim 18, further comprising securing a third fixation fastener within a third fixation hole of the bone plate and to the first bone portion.

20. The method as recited in claim 18, wherein the first engagement feature of the first reduction fastener comprises a neck of reduced diameter.

21. The method as recited in claim 18, wherein the first and second reduction fasteners comprise screws.

22. The method as recited in claim 18, wherein the first and second reduction fasteners comprise wires.

23. The method as recited in claim 18, further comprising locking the compression clamp, thereby locking a position of the second bone portion relative to the first bone portion.

24. The method as recited in claim 18, wherein engaging the first engagement member of the compression clamp with the first engagement feature of the first reduction fastener comprises positioning a first hook at least partially about a portion of the first engagement feature that is positioned above the bone plate.

25. The method as recited in claim 24, wherein engaging the second engagement member of the compression clamp with the second engagement feature of the second reduction fastener comprises positioning a second hook at least partially about a portion of the second engagement feature that is positioned above the bone plate.

26. The method as recited in claim 18, wherein securing the second reduction fastener within an elongated slide channel of the bone plate and to the second bone portion comprises advancing the second reduction fastener until a rounded shoulder of the second reduction fastener engages the elongated slide channel.

27. A method of surgically repairing bone, comprising:
placing a bone plate across a bone discontinuity;
securing a first reduction fastener within a first fixation hole of a bone plate and to a first bone portion, the first reduction fastener comprising a wire;
securing a second reduction fastener within an elongated slide channel of the bone plate and to a second bone portion, the second reduction fastener comprising a wire;
positioning a first engagement member of a compression clamp about an exterior surface of the first reduction fastener;
positioning a second engagement member of the compression clamp about an exterior surface of the second reduction fastener;
closing the compression clamp by manually squeezing together handles of the compression clamp, thereby drawing the second reduction fastener and the second bone portion along the elongated slide channel toward the first reduction fastener and the first bone portion; and
securing a fixation fastener within a second fixation hole of the bone plate and to the second bone portion.

28. The method as recited in claim 27, wherein securing the second reduction fastener within the elongated slide channel of the bone plate and to the second bone portion comprises advancing the second reduction fastener until a rounded shoulder of the second reduction fastener engages the elongated slide channel.

29. The method as recited in claim 28, further comprising locking the compression clamp, thereby locking a position of the second bone portion relative to the first bone portion.

30. The method as recited in claim 29, wherein positioning the first engagement member of the compression clamp about the exterior surface of the first reduction fastener comprises positioning a first hook at least partially about a portion of a first engagement feature of the first reduction fastener that is positioned above the bone plate.

31. The method as recited in claim 30, wherein positioning the second engagement member of the compression clamp about the exterior surface of the second reduction fastener comprises positioning a second hook at least partially about a portion of a second engagement feature of the second reduction fastener that is positioned above the bone plate.

32. The method of claim 31, further comprising securing a third fixation fastener within a fixation hole of the bone plate and to the first bone portion.

33. A method of surgically repairing bone, comprising:
placing a bone plate across a bone discontinuity;
temporarily securing the bone plate to one or more of a first bone portion and a second bone portion by inserting one or more wires through one or more attachment holes in the bone plate and into one or more of the first bone portion and the second bone portion;
securing a first reduction fastener within a first fixation hole of a bone plate and to the first bone portion;
securing a second reduction fastener within an elongated slide channel of the bone plate and to the second bone portion;
positioning a first engagement member of a compression clamp about an exterior surface of the first reduction fastener;
positioning a second engagement member of the compression clamp about an exterior surface of the second reduction fastener;
closing the compression clamp by manually squeezing together handles of the compression clamp, thereby drawing the second reduction fastener and the second bone portion along the elongated slide channel toward the first reduction fastener and the first bone portion; and
securing a fixation fastener within a second fixation hole of the bone plate and to the second bone portion.

34. The method of claim 33, further comprising:
removing the first reduction fastener and the second reduction fastener from the bone plate; and
securing an additional fixation fastener within the first fixation hole and to the first bone portion.

35. The method of claim 33, wherein positioning the first engagement member about an exterior surface of the first reduction fastener comprises causing the first engagement member to pivot relative to the compression clamp.

36. The method of claim 33, wherein positioning the first engagement member about an exterior surface of the first reduction fastener comprises positioning the first engagement member about a neck of the first reduction fastener.

37. The method of claim 33, wherein the first and second reduction fasteners comprise wires.

38. A method of surgically repairing bone, comprising:
placing a bone plate across a bone discontinuity;
securing a first reduction fastener within a first fixation hole of a bone plate and to a first bone portion such that a first engagement feature of the first reduction fastener is positioned above the bone plate, the first reduction fastener comprising a wire;
securing a second reduction fastener within an elongated slide channel of the bone plate and to a second bone portion such that a second engagement feature of the second reduction fastener is positioned above the bone plate, the second reduction fastener comprising a wire;
engaging a first engagement member of a compression clamp with the first engagement feature of the first reduction fastener;
engaging a second engagement member of the compression clamp with the second engagement feature of the second reduction fastener;
closing the compression clamp by manually squeezing together handles of the compression clamp, thereby drawing the second reduction fastener and the second bone portion along the elongated slide channel toward the first reduction fastener and the first bone portion; and
securing a fixation fastener within a second fixation hole of the bone plate and to the second bone portion.

39. The method as recited in claim 38, further comprising locking the compression clamp, thereby locking a position of the second bone portion relative to the first bone portion.

40. The method as recited in claim 39, wherein engaging the first engagement member of the compression clamp with the first engagement feature of the first reduction fastener comprises positioning a first hook at least partially about a portion of the first engagement feature that is positioned above the bone plate.

41. The method as recited in claim 40, wherein engaging the second engagement member of the compression clamp with the second engagement feature of the second reduction fastener comprises positioning a second hook at least partially about a portion of the second engagement feature that is positioned above the bone plate.

42. The method as recited in claim 41, wherein securing the second reduction fastener within the elongated slide channel of the bone plate and to the second bone portion comprises advancing the second reduction fastener until a rounded shoulder of the second reduction fastener engages the elongated slide channel.

\* \* \* \* \*

UNITED STATES PATENT AND TRADEMARK OFFICE
CERTIFICATE OF CORRECTION

PATENT NO. : 8,162,996 B2  
APPLICATION NO. : 12/607870  
DATED : April 24, 2012  
INVENTOR(S) : Schelling et al.

Page 1 of 1

It is certified that error appears in the above-identified patent and that said Letters Patent is hereby corrected as shown below:

On the Title Page
Item (56), U.S. Patent Documents, change "6/2004    Jones et al." to --8/2004    Jones et al.--
Item (56), U.S. Patent Documents, change "Assaker et al. ............606/69" to
   --Assaker et al. ............606/069--

Title Page 2
Item (56), U.S. Patent Documents, change "Strnad et al." to --Stmad et al.--

In the Specification

Column 8
Line 3, change "implementations;" to --implementations--
Line 44, change "11a-11i" to --100a-100i--

Column 9
Line 42, change "engagement grooves 510" to --engagement grooves 518--

Column 10
Line 41, change "bone screws" to --bone screw--
Line 63-64, change "reduction fastener 600" to --fixation fastener 600--

Column 11
Line 2, change "reduction fastener 600" to --fixation fastener 600--

Column 15
Line 18, change "fi portion 902" to --first portion 902--

Signed and Sealed this
Sixteenth Day of December, 2014

Michelle K. Lee
*Deputy Director of the United States Patent and Trademark Office*